(12) United States Patent
Cornelius et al.

(10) Patent No.: US 6,645,471 B2
(45) Date of Patent: Nov. 11, 2003

(54) COMPOSITE ABRASIVE MATERIAL FOR ORAL COMPOSITIONS, AND METHODS OF MAKING AND USING SAME

(75) Inventors: John M. Cornelius, Forest Hill, MD (US); Michel J. Martin, Plainsboro, NJ (US)

(73) Assignee: J. M. Huber Corporation, Edison, NJ (US)

( * ) Notice: Subject to any disclaimer, the term of this patent is extended or adjusted under 35 U.S.C. 154(b) by 0 days.

(21) Appl. No.: 09/986,309

(22) Filed: Nov. 8, 2001

(65) Prior Publication Data

US 2003/0124069 A1 Jul. 3, 2003

(51) Int. Cl.$^7$ .............. A61K 7/16; C09C 1/28
(52) U.S. Cl. ............. 424/49; 51/308; 424/57; 423/335; 423/339
(58) Field of Search .......... 51/308; 423/339; 424/49, 57

(56) References Cited

U.S. PATENT DOCUMENTS

| | | | | |
|---|---|---|---|---|
| 3,650,783 A | * | 3/1972 | Yates | 501/128 |
| 3,819,526 A | * | 6/1974 | Pierce et al. | 510/442 |
| 3,894,572 A | * | 7/1975 | Moore | 427/135 |
| 4,077,897 A | * | 3/1978 | Gault | 252/99 |
| 4,276,326 A | * | 6/1981 | Joshi | 427/220 |
| 4,330,424 A | * | 5/1982 | Joshi | 252/135 |
| 4,421,527 A | | 12/1983 | Wason | |
| 4,515,772 A | | 5/1985 | Parran, Jr. et al. | |
| 4,767,570 A | * | 8/1988 | Joubert | 257/540 |
| 4,806,340 A | | 2/1989 | Gaffar et al. | |
| 5,185,155 A | * | 2/1993 | Behan et al. | 424/451 |
| 5,334,741 A | * | 8/1994 | Quin et al. | 558/110 |
| 5,500,223 A | * | 3/1996 | Behan et al. | 424/451 |
| 5,676,932 A | | 10/1997 | Wason et al. | |
| 5,869,028 A | | 2/1999 | McGill et al. | |
| 5,891,421 A | | 4/1999 | McGill et al. | |
| 6,214,383 B1 | | 4/2001 | Esch et al. | |
| 6,221,430 B1 | * | 4/2001 | Tompsett | 427/212 |
| 6,238,648 B1 | | 5/2001 | Leusch et al. | |
| 6,277,408 B1 | * | 8/2001 | Wellinghoff et al. | 424/473 |

FOREIGN PATENT DOCUMENTS

| | | | |
|---|---|---|---|
| AU | 199727045 B2 | | 12/1997 |
| EP | 75 250 | * | 3/1983 |
| JP | 092 48450 | * | 9/1997 |

OTHER PUBLICATIONS

Michel More et al HCAPLUS 135:95478 (425149:2001) Adsorption of Polyphosphates onto the Surfaces of Silica Particles, 1999.*

Uejima et al HCAPLUS 127: 298143 (640355: 1997) Porous Synthetic Silica Particles Containing Disodium Hydrogen Phosphate Trisodium Phosphate Dipotassium Hydrogen Phosphate Tripotassium Phosphate etc, 1997.*

Quin et al HCAPLUS 109: 12699 (412699: 1998 J. Chem. Soc. Chem. Commun. 8: 555–556 (1988) Phosphorylation of the Surface of Silica Gel by Ethyl Metaphosphate.*

Morton Pader, "Oral Hygiene Products and Practice", Product Components: Therapeutic Agents, pp. 365–368, Marcel Dekker, Inc.

* cited by examiner

*Primary Examiner*—Shep K Rose
(74) *Attorney, Agent, or Firm*—Carlos Nieves; Raymond Hoch

(57) ABSTRACT

A composition of matter comprising particles of silica, where the silica particles have surfaces at which condensed phosphate is retained, and a production methodology therefor. Oral compositions containing this composition of matter are also presented, which are endowed with enhanced cleaning efficacy.

9 Claims, 2 Drawing Sheets

COMPOSITE ABRASIVE MATERIAL FOR ORAL COMPOSITIONS, AND METHODS OF MAKING AND USING SAME

TECHNICAL FIELD

The present invention relates to composite abrasive materials, and particularly composite abrasive materials of silicas and chemical cleaning agents that are useful in oral compositions, and which provide enhanced chemical cleaning action on teeth to add improved anti-calculus effect, as well as methods of producing and using such composite materials.

BACKGROUND OF THE INVENTION

Modern dentifrices often contain an abrasive substance for controlled mechanical cleaning and polishing of teeth, and optionally a chemical cleaning agent, among other common ingredients, such as humectants, flavors, therapeutic ingredients, such as a fluoride source, rheology control agents, binders, preservatives, colors, and sudsing agents, among others.

The primary function of an abrasive substance in such dentifrice formulations is to help remove various deposits including pellicle film from the surface of teeth. Pellicle film is tightly adhered and often contains brown or yellow constituents, which impart an unsightly appearance to the teeth. However, while cleaning is important the abrasive typically is selected so as not to be overly abrasive as to damage hard tissues of teeth.

As the abrasive material, synthetically produced amorphous precipitated silicas have played an important role as an ingredient in many contemporary dentifrice formulations. In addition to their cleaning ability, they are also safe, nontoxic, and compatible with other standard dentifrice ingredients, such as glycerin, sorbitol (or xylitol), thickening agents, detergent coloring and fragrance materials and, optionally, fluoride and other therapeutically active compositions.

Synthetic amorphous precipitated silicas are generally prepared by admixing alkaline silicate solutions with acids, stirring and then filtering out the precipitated silica. The resulting precipitate is next washed, dried, and often comminuted to a desired size. When preparing synthetic precipitated silicas, the objective is to obtain silicas, which provide maximal cleaning with minimal damage to oral (hard) tissues of the teeth. Dental researchers are continually concerned with identifying precipitated silicas meeting these objectives. Examples of the many patented publications describing such precipitated silicas include U.S. Pat. Nos. 4,122,161, 5,279,815 and 5,676,932 to Wason et al., and U.S. Pat. Nos. 5,869,028 and 5,981,421 to McGill et al.

As prior chemical cleaning agents for teeth, alkali metal salts of tartaric acid, citric acid, and soluble pyrophosphates have been added neat (as a separate ingredient from the abrasive) during the actual formulating of the dentifrice composition. Chemical cleaning agents include water soluble salts that are thought to chelate calcium ions as a mechanism for inhibiting calculus formation on teeth. As explained in U.S. Pat. Nos. 4,806,340 and 4,515,772, dental calculus, or tartar as it often is referred, is a hard, mineralized deposit which forms on the surfaces of teeth, especially at the gingival margin. Mature calculus is formed on the teeth when crystals of calcium phosphates begin to be deposited in the pellicle and extracellular matrix of the dental plaque and become sufficiently closely packed together for the aggregates to become resistant to deformation. The resulting crystalline calculus material is arranged in a hydroxyapatite crystal lattice structure, but an organic portion is also present including epithelial cells, food debris, microorganisms, and so forth.

Chelating agents, such as certain pyrophosphates, have been added neat to dentifrices in efforts to chelate calcium ions found in the cell walls of the bacteria on teeth and also disrupt, inhibit and reduce plaque and calculus formation by removing calcium from the calcium bridges which help hold the calculus biomass intact. As with the abrasives, the chelating agents, should not be too aggressive. A chelating agent having too high an affinity for calcium may cause undesired tooth demineralization.

Thus, an effective dentifrice formulation should maximize pellicle film removal without causing undue abrasion or demineralization of the hard teeth tissue. According to U.S. Pat. Nos. 5,869,028 and 6,238,648, and Pader, M., Oral Hygiene Products and Practice, Marcel Dekker, Inc., New York, 1988, pp. 365–368, an effective amount of pyrophosphate salt added neat to conventional dentifrices in efforts to impart such chemical cleaning effects has been considered to be enough to provide at least about 1.0% free pyrophosphate ions, and an amount in the range of about 1.5–2.0% to about 6% is often preferred. According to U.S. Pat. No. 6,238,648, the pyrophosphates can be added to dentifrices in their anhydrous or hydrated forms, and may be present predominantly dissolved, predominantly undissolved, or as a mixture of those physical states.

The cleaning properties of dentifrice compositions on teeth are typically expressed in terms of Pellicle Cleaning Ratio (PCR) described by Stookey, et al., J. Dent. Res., 61, 1236–1239, and Hefferren, J. J., J. Dent. Res., 37, 563–573. However, the traditional PCR test was developed at a time when chemical cleaning agents were not used in dentifrice formulations.

Generally speaking, the PCR test begins with a biological film applied to extracted bovine teeth and the tooth is kept moist until tested. The brightness (L value) of each tooth is measured after the stain is applied. The teeth are then brushed with a slurry of the sample toothpaste. After brushing, the brightness of each tooth is again measured and the difference in values (ΔL) used to determine the cleaning effectiveness of the toothpaste.

The primary measure of cleaning in the PCR test is the result of mechanical cleaning. The abrasiveness of the toothpaste is measured. The abrasiveness of the toothpaste results from the silica, calcium phosphate, alumina, or other solid particles in the toothpaste mechanically removing the film on the bovine teeth used in the test. In general, the type of stain used and the duration of the brushing in the PCR does not allow for sufficient contact time for chemical cleaning to occur.

As noted previously, the conventional method for incorporating chemical cleaning agents in oral cleaning compositions, such as toothpaste, is to add them as separate ingredients during the formulating of the toothpaste. However, in spite of the many prior disclosures relating to compositions for oral cleaning and antiplaque activity in this respect, there is still a need for oral cleaning compositions providing combined and improved effects of pellicle cleaning and calculus inhibition.

Accordingly, it is an object of the present invention to provide chemical cleaning agents adapted for use in oral cleaning compositions in a manner which can impart improved effects of pellicle cleaning and calculus inhibition.

Another object of the present invention is to provide an abrasive cleaning material useful for preventing or removing tooth stains, and thereby whitening teeth. A further object of the present invention is to provide an abrasive cleaning material useful for preventing or removing plaque from teeth. It is yet another object of the invention to provide an abrasive cleaning material having chemical cleaning functionality that is useful in oral cleaning compositions as well as being generally useful in other types if cleaning applications. These and other objects will become readily apparent from the disclosure which follows.

SUMMARY OF THE INVENTION

The present invention relates to a composition of matter comprising particles of silica characterized by the silica particles having surfaces at which condensed phosphate is retained. The silica surfaces at which the condensed phosphate is retained on the silica particles comprise land areas, surface pores, or both. For purposes herein, this composition of matter is often referred to as surface-modified silica particles of the invention.

Among other things, the surface-modified silica particles of this invention impart enhanced chemical cleaning, stain removal, anti-calculus, and/or antiplaque properties when incorporated into oral cleaning compositions, to yield a significant increase and improvement in teeth whitening.

In one aspect, the silica used as the substrate that is surface-modified by the condensed phosphate can be precipitated silica or silica gel. In another aspect, the condensed phosphate is one or a combination of tetraalkali metal pyrophosphate, dialkali metal diacid pyrophosphate, trialkali metal monoacid pyrophosphate, pentaalkali metal tripolyphosphate, and alkali metal polymetaphosphate. In one preferred aspect, the condensed phosphate is one or a combination of tetrasodium pyrophosphate, tetrapotassium pyrophosphate, disodium dihydrogen pyrophosphate, trisodium monohydrogen pyrophosphate, pentasodium tripolyphosphate and sodium polymetaphosphate, singly or in combinations thereof.

In a further aspect, the surface-modified silica of this invention comprises about 30 to about 99.9 wt % silica and from about 0.1 to about 70 wt % condensed phosphate deposited at the silica surfaces. In one further aspect, the surface-modified silica of this invention comprises about 60 to about 95 wt % silica and from about 5 to about 40 wt % condensed phosphate. In yet another aspect, the surface-modified silica particles of this invention have an average particle size value ranging from about 0.1 to about 80 μm.

In another aspect, the present invention provides a method for producing such surface-modified silica particles in which the solid silica substrate particles to be surface-modified are produced by acidulation of an alkali metal silicate. The crude silica particles obtained are then contacted with the condensed phosphate salt as dissolved in an aqueous medium. The silica continues to be solid particles during this mixing. This water-containing mixture is dried effective to form silica-based particles having surface-modification due to the presence (association) of the condensed phosphate in the mixture. In a preferred embodiment, the silica particles are not dried to a water content of less than about 15 wt % water until after being bathed with the aqueous solution containing the dissolved cleaning agent. In one preferred implementation of this embodiment, the drying of the surface-modified silica is performed by spray drying.

The resulting dried, surface-modified silica particles of the method of this invention are freely-flowable in bulk form, and are stable in a dry or wet state. In the dried state, the particles can be stably stored and shipped as needed for later use when desired in formulating an oral cleaning composition, such as a toothpaste. Even after the modified silica particles are actually incorporated into a dentifrice composition, the resulting dentifrice formulations are observed to have sufficiently long shelf lives for practical usage. The dried cleaning agent deposits on the silica surfaces are retained until released during brushing. The association and retention thereof is substantially retained intact thereon even after numerous months of presence in a water-containing dentifrice.

Another advantage gained by the surface-modified silica particles made according to this invention is that lower concentrations of the cleaning agent, that is, the condensed phosphates, can be used to provide equivalent cleaning in a dentifrice as compared to that of dentifrices using higher concentrations of the same cleaning agent except as added in the conventional neat (free) form.

The oral cleaning compositions that can be benefited by incorporation of the surface-modified silica particles of this invention include, for example, liquid dentifrices, toothpastes, chewing gums and mouthwashes, and the like. The surface-modified silica particles of the invention also have wider cleaning utility and application, including, for instance, as a metal, ceramic or porcelain cleaning or scrubbing agent.

DETAILED DESCRIPTION OF THE PREFERRED EMBODIMENTS

Figure 1:
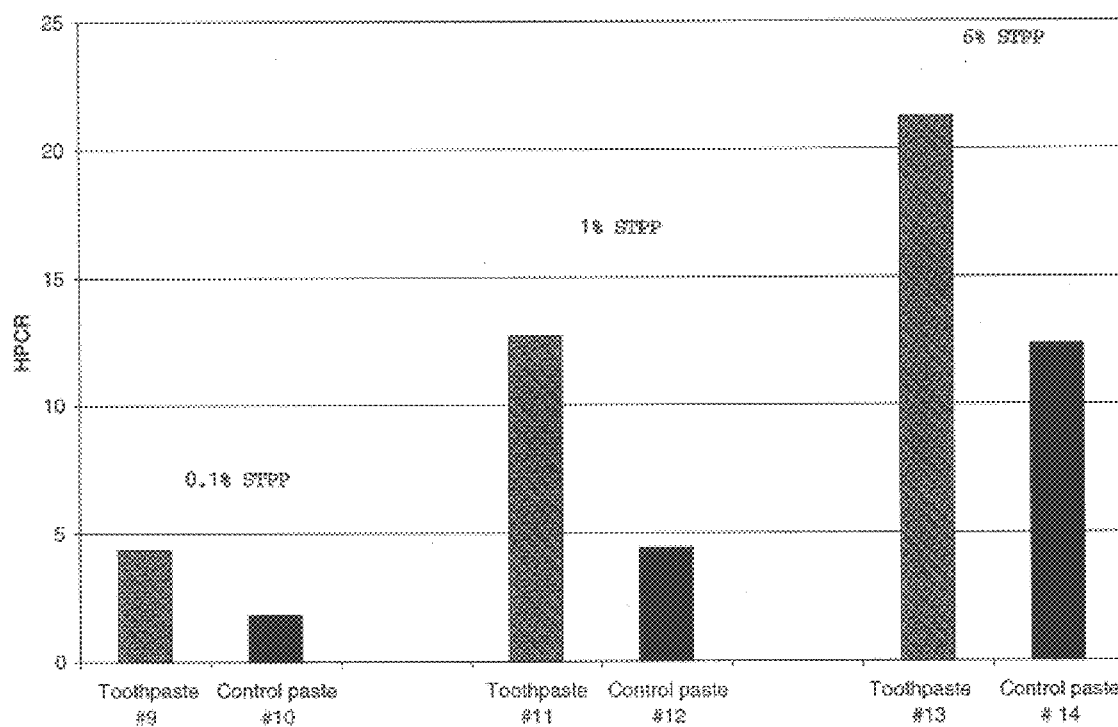
FIG. 1 includes bar graphs showing the results of certain experimental studies described in the examples herein comparing the cleaning action observed for a dentifrice containing the surface-modified silica according to an aspect of this invention versus dentifrices containing the cleaning agent in free form only.

The present invention provides a new class of composite abrasive cleansing particles including amorphous silicas in the form of a precipitated, gelled or colloidal amorphous silica materials, which have a chemical cleaning agent introduced and retained onto lands and/or into pores at the exterior exposed surfaces of the silicas. These composite abrasive cleaning particles are physically robust and sufficiently stable for practical usage in oral cleaning compositions. The invention also encompasses oral cleaning compositions containing these abrasive cleaning particles, as well as methods of making such oral cleaning compositions and methods of using them to clean teeth.

Silica particles have condensed phosphate solids retained at exterior surfaces of the silica particles as a result of a mixing and drying procedure performed on those particular ingredients to form a silica surface-modified with a chemical cleaning agent. This surface-modification of silica is performed separate and prior to the actual formulating of a dentifrice incorporating the silica.

The condensed phosphate cleaning agents used are water soluble salts in their free state. However, once associated with surfaces of the silica particles by use of production techniques of this invention, the solubility of the cleaning agent retained on the surfaces of the silica particles is significantly reduced such that the resulting composite particles have a practically-useful shelf life in dentifrices. Namely, the condensed phosphate chemical cleaning agent is sufficiently. firmly retained at the surfaces of the silica particles themselves in this invention such that the resulting surface-modified, composite particles are robust enough to tolerate storage, transportation, handling and dentifrice formulation. The mechanical rubbing action exerted between the surface-modified silica, as incorporated into a dentifrice, and the surface of teeth presses the retained condensed phosphate solids intimately, directly and assuredly against the teeth. As a consequence, when rubbed against teeth during brushing, the cleaning agent deposits provided on the silica surfaces effectively remove stains and inhibit or reduce calculus formation on teeth, among other things, to provide improved teeth whitening.

For purposes herein, the following terms have the indicated meanings.

By "wet cake" it is meant a wet mass of silica particles that has been prepared by the precipitation of the reaction product of the acidulation of sodium silicate that is washed with water to remove residual salts, and then filtered to remove a large portion of the water content.

By "cleaning agent" or "chemical cleaning agent" it is meant any soluble salt of the polyphosphate family including, but not limited to alkali metal salts of condensed phosphates such as tetrasodium pyrophosphate, tetrapotassium pyrophosphate, disodium dihydrogen pyrophosphate, trisodium monohydrogen pyrophosphate, sodium tripolyphosphate, sodium polymetaphosphate, and or other chemical agent imbuing a dentifrice with comparable cleaning functionality as described herein.

By "slurry" it is meant an aqueous mixture of water and at least one other particulate silica component suspended therein, wherein water forms the continuous phase.

By "dentifrice" it is meant oral care products such as, without intending to be limiting, toothpastes, tooth powders, and denture creams.

By "incorporating" it is meant that the chemical cleaning agents are put into solution with water and mixed with silica, and the resulting slurry is then dried by any suitable means, such as spray drying.

A test for determining the efficacy of the chemical cleaning action of oral cleaning compositions, such as dentifrices, on teeth is simulated using a modified version of the PCR test, which modified test is referred to herein as the "Huber" Pellicle Cleaning Ratio Test ("HPCR"). The protocol retained with the HPCR test is described in more detail below.

The following descriptions describe several preferred, non-limiting illustrative embodiments of the present invention. The inventive surface-modified silica endowed with enhanced chemical cleaning properties, as well as a method for producing the silicas, will first be discussed in more detail.

In one implementation of the invention, silica dental abrasives are combined with the chemical cleaning agent after precipitation of crude silica, by mixing of the crude silica with a solution containing solubilized (dissolved) condensed phosphate, and drying the mixture to produce the modified silica particulate material of this invention having enhanced tooth cleaning capabilities.

The chemical cleaning agents used in this regard are water soluble salts of condensed phosphates. The condensed phosphates should be those that can chelate or complex calcium ions, thereby inhibiting calculus formation on teeth, when used in oral cleaning compositions according to this invention. These cleaning agents are able to complex calcium or other cationic species found in the cell walls of the bacteria on teeth and also disrupt plaque by removing calcium from the calcium bridges which help hold this biomass intact.

A wide variety of water soluble salts of condensed phosphates can be used in the practice of this invention in forming the solid deposits of cleaning agent on the surfaces of the silica particles. In one preferred aspect, water-soluble alkali metal salts of condensed phosphates are suitable as the cleaning agent material. Examples of such water-soluble alkali metal salts of condensed phosphates include, but are not limited to, tetraalkali metal pyrophosphate, dialkali metal diacid pyrophosphate, trialkali metal monoacid pyrophosphate, water soluble polyphosphates, such as pentaalkali metal tripolyphosphates, or water soluble alkali metal polymetaphosphates, singly or in combinations thereof. The alkali metals in these salts of condensed phosphates preferably are sodium or potassium.

Specific examples of useful condensed phosphates in this regard include, for instance, tetrasodium pyrophosphate (often abbreviated as "TSPP" herein) ($Na_4P_2O_7$), tetrapotassium pyrophosphate ("TKPP") ($K_4P_2O_7$), disodium dihydrogen pyrophosphates ("DDPP") ($Na_2H_2P_2O_7$), trisodium monohydrogen pyrophosphate ("TMPP") ($Na_3HP_2O_7$), pentasodium tripolyphosphate ("STPP") ($Na_5P_3O_{10}$), sodium metaphosphate ("SMP"){$(NaPO_3)_3$ where x is a positive integer such as six}. These condensed phosphates can be used either singly or in mixtures thereof.

These types of pyrophosphates and polyphosphates salts can be obtained as alkali metal salts of polyacids made from known condensation reactions involving orthophosphoric acid. Pyrophosphoric acids, for instance, are described in more detail in Kirk & Othmer, Encyclopedia of Chemical Technology, 4th Ed., Vol. 18, Interscience Publishers (1996), incorporated herein by reference.

The soluble condensed phosphates can be used in their anhydrous or hydrated forms as the starting material dissolved into an aqueous solution into which the silica particles also are added, mixed and then dried in the surface-modification treatment procedure performed on the silica. For instance, the decahydrate forms of TSPP or TKPP, or the hexahydrate forms of DDPP or STPP, optionally could used as the condensed phosphate salt ingredient used in the surface-modification (pre)treatment of the silica particles, as the substrates, prior to formulating the dentifrice.

Crude, undried liquid phase silicas are preferred materials as the particulate silica substrate material that is surface-modified with chemical cleaning agent material according to an aspect of this invention. Liquid phase silicas include amorphous precipitated silicas, silica gels or hydrogels and colloidal silicas produced by acidulating an alkali metal silicate with a mineral acid, such as sulfuric acid, or organic acid. For instance, the crude silica to be used as the substrate for surface-modification treatment can be, for example, precipitated silicas, such as those described in the earlier mentioned U.S. patents to Wason et al. and McGill et al., which teachings are incorporated herein by reference, or gelled silicas such as described in U.S. Pat. No. 3,538,230 to Pader ("xerogels"), also incorporated herein by reference, among other types of synthetic particulate silicas.

Preferably, the crude silica is precipitated from alkali metal silicate solution by an acid, such as a mineral acid, with heating. Useful techniques for conducting the precipitation (acidulation) reaction itself to produce crude homogenous amorphous silica particles are widely known and understood. The resulting silica is filtered and washed to provide a wet cake of crude silica, in manners such as customarily practiced. Wet cake of silica generally contains about 40 wt % to about 60 wt % water, and the remainder is principally solids.

The precipitated reaction mass generally is filtered and washed with water to reduce the $Na_2SO_4$ levels to tolerable levels. Washing of the reaction product is generally conducted after filtering. The pH of the washed wet cake can be adjusted, if necessary, prior to proceeding to subsequent steps described herein.

At about this juncture of the process, there is a dramatic departure made from customary silica production.

Namely, after precipitation, filtration, and any washing, the crude silica product obtained is dispersed in an aqueous medium containing a suitable dissolved amount of a condensed phosphate salt of the types indicated herein. The resulting mixture is gently agitated or mixed, such as with a paddle mixer, for a sufficient period of time to ensure that dissolved condensed phosphates and silica particles are substantially uniformly dispersed.

Thereafter, the dispersion of wet cake is dried by any conventional means, such as spray drying. The concentration of the dissolved condensed phosphate mixed with the silica particles is adjusted effective to provide, in the dried surface-modified silica product, particles comprising generally about 30 to about 99.9 wt % silica and from about 0.1 to about 70 wt % condensed phosphate, and particularly, about 60 to about 95 wt % silica and from about 5 to about 40 wt % condensed phosphate. The amount of water containing dissolved condensed phosphate is adjusted to achieve 15 to 40 wt. % solids, when added to the silica wetcake. Therefore, the concentration of condensed phosphate in the aqueous dilution solution is adjusted to achieve the desired amount of condensed phosphate in the final surface-modified silica product and the desired solids content for drying.

Drying can be effected by any conventional equipment used for drying silica, e.g., spray drying, nozzle drying (e.g., tower or fountain), flash drying, rotary wheel drying or oven/fluid bed drying. The dried silica product generally should have a 2 to 15 wt. % moisture level. The nature of the silica reaction product and the drying process both are known to affect the density and liquid carrying capacity. Further, care must be taken that the drying operation and subsequent operations do not detrimentally affect the structure of the silica obtained in the precipitation stage. Preferably, the mixture of the crude silica particles and dissolved condensed phosphate in the aqueous medium is spray dried. For example, rotary wheel spray dried surface modified-silica product of this invention generally has an average particle size of 20 to 100+$\mu$m. The dried surface-modified silica product is in a finely divided form.

In one preferred embodiment, the water content of the precipitated silica-containing fractions is about 25% by weight or more for all times until the drying procedure is performed on the surface-modified silica particles.

To decrease the size of the dried surface-modified silica particles further, if desired, conventional grinding and milling equipment can be used. A hammer or pendulum mill may be used in one or multiple passes for comminuting and fine grinding can be performed by fluid energy or air-jet mill. Products ground to the desired size may be separated from other sizes by conventional separation techniques, e.g., cyclones, classifiers or vibrating screens of appropriate mesh sizing, and so forth.

The resulting surface-modified silica abrasive polishing agent material generally has an average particle size ranging between about 0.1 to about 80 microns, and preferably in one embodiment ranges between about 0.1 and about 30 microns. The mean particle size of the silicas is measured as "MPS"using a Microtrac II Particle Analyzer manufactured by Leeds and Northrup. The MPS values provided herein are mean values ("50%") unless otherwise indicated.

Silicas used in accordance with this invention preferably have mercury intrusion void volume values in the range of about 1.0 to about 4.0 cc/g, as determined using an Autopore II 9220 Porosimeter by Micromeritics Corporation.

In an alternative implementation of the invention, the crude silica particles that are to be surface-modified with the chelating agent according to this invention can be commercially available precipitated or gelled silicas, such as Zeodent® 113, Zeodent® 115, Zeodent® 623, Zeodent® 124 silicas, and so forth, which are available from J. M. Huber Corporation. After dispersing the silicas in an aqueous medium containing solubilized condensed phosphate, the mixture is spray dried in a similar manner as the treatment performed on the crude freshly prepared silicas, such as present in wet cake. However, this alternative would necessitate multiple drying operations being performed on the silica, which would increase drying costs.

Other Oral Cleaning Composition Additives:

A pharmaceutically acceptable carrier for the components of the compositions of the present invention is optional and can be any dentifrice vehicle suitable for use in the oral cavity. Such carriers include the usual components of toothpastes, tooth powders, prophylaxis pastes, lozenges, gums, and the like and are more fully described thereafter.

Flavoring agents optionally can be added to dentifrice compositions. Suitable flavoring agents include oil of Wintergreen, oil of peppermint, oil of spearmint, oil of sassafras, and oil of clove. Sweetening agents, which can be used, include aspartame, acesulfame, saccharin, dextrose, levulose and sodium cyclamate. Flavoring and sweetening agents are generally used in dentifrices at levels of from about 0.005% to about 2% by weight A water-soluble fluoride compound optionally can be added and present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, act 20,1970 to Briner et al. and U.S. Pat. No. 3,678,154, Jul. 18, 1972 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes and dentifrices according to another embodiment of this invention. Water employed in the preparation of suitable toothpastes should preferably be deionized and free of organic impurities. Water generally comprises from about 2% to 50%, preferably from about 5% to 20%, by weight, of the toothpaste compositions. These amounts of water include the free water which is added plus that which is introduced with other additives and materials, such as humectant.

In preparing toothpastes, it often is necessary to add some thickening or binder material to provide a desirable consistency and thixotropy. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gun, gum arabic, and gum tragacanth can also be used. Thickening agents in an amount from about 0.5% to about 5.0% by weight of the total composition generally can be used.

Silica thickeners can also be used to modify toothpaste rheology. Precipitated silica, silica gels and fumed silica can be used. Silica thickeners can be added generally at a level of about 5% to about 15%.

It is also often desirable to include some humectant material in a toothpaste to keep it from hardening. Suitable humectants include glycerin (glycerol), sorbitol, polyalkylene glycols such as polyethylene glycol and polypropylene glycol, hydrogenated starch hydrolyzates, xylitol, lactitol, hydrogenated corn syrup, and other edible polyhydric alcohols, used singly or as mixtures thereof. Suitable humectants can be added generally at a level of from about 15% to about 70%.

Other chelating agents optionally can be added neat to the dentifrices of the invention, such as alkali metal salts of tartaric acid and citric acid.

Although alkali metal salts of pyrophosphates or polyphosphates can be added neat to the dentifrice, they are not required or necessary if sufficient amounts of the condensed phosphate are present as solid integral deposits at the surfaces of silica particles modified according to this invention (which generally only needs to be a relatively low amount).

Other optional ingredients and adjuvants of dentifrices, such as those described in U.S. Pat. No. 5,676,932 for instance, also can be added as needed or desired. These other optional adjuvants, additives, and materials that can be added to the dentifrice compositions of the present invention include, for example, foaming agents (e.g., sodium lauryl sulfate), detergents or surfactants, coloring or whitening agents (e.g., titanium dioxide, FD&C dyes), preservatives (e.g., sodium benzoate, methyl paraben), chelating agents, and other materials that can be used in dentifrice compositions. The optional additives, if present, generally are present in small amounts, such as no greater than about 6% by weight each.

Although not desirous of being bound to any specific theory at this time regarding the underlying mechanism, the inventive method is thought to result in numerous deposits of solid condensed phosphate material forming as a partial or continuous surface coating on the surfaces of the silica product, whether they are associated with and retained at the land (exterior non-pore) surfaces of the silica particles and/or as retained in the pores present in the surface of the silica particles. These solid deposits of the condensed phosphate at the silica particle surfaces are directly, forcefully and intimately delivered against the tooth surface during brushing using a dentifrice containing the surface-modified silica. As a result, increased and superior tooth cleaning and stain removal is achieved, such as can be confirmed by certain pellicle cleaning ratio tests described herein.

Additionally, while the usefulness of the abrasive cleaning material of this invention is specifically illustrated in oral cleaning compositions, it is will be appreciated that the surface-modified silica of this invention has wider usefulness. For instance, it can be used in metal, ceramic or porcelain cleaning or scrubbing.

The following non-limiting examples will further illustrate the present invention. All parts, ratios, concentrations, and percentages are based upon weight unless otherwise specified.

EXAMPLES

EXAMPLE 1

To prepare a control precipitated silica, 515 gallons of sodium silicate, 13.0% (2.65 mole ratio) solution are added to a steam-jacketed reactor, which is equipped with high shear mixing blades, and heated to 190° F. After the reactor reaches the desired temperature, 13.0% silicate solution preheated to 185 F. and 11.4% sulfuric acid solution at ambient temperature are added simultaneously at a rate of 102.9 and 45.2 gpm, respectively. Simultaneous addition of the silicate and acid continues for 47 minutes with agitation. After 47 minutes the sodium silicate addition is stopped, while the acid addition continues until the reaction mixture reaches a pH of 5.8 to 6.0. When the pH reaches 5.8 to 6.0, the temperature of the reaction media is increased to 199° F. for 20 minutes, while maintaining the pH. Thereafter, the resultant precipitated silica reaction mass is transferred to a rotary drum filter for filtration and washing. This dewatered material is referred to as a "wet cake". The silica wet cake, containing abrasive silica with an Einlehner abrasion value of 6.6 mg, was adjusted to a solids content of 15% with water as the diluent. The resulting silica slurry was spray dried in an ANHYDRO spray drier with an inlet temperature of 350° C. and then milled in a Jet Pulveriser air mill to a mean particle size of 8.7 $\mu$m. The resulting silica was then formulated into toothpaste, as described in Table 2 below.

To determine the chemical cleaning effect of the toothpaste, an HPCR cleaning test was conducted. The results of the HPCR test are given in Table 3.

The HPCR test method, for purposes herein, used to determine the chemical cleaning effectiveness of the oral composition containing the abrasive material and any cleaning agents, and so forth, is described as follows.

To prepare a staining concoction, a 250 ml beaker containing a magnetic stir bar is added with stirring 50 ml of deionized water, 1.00 g of Folgers Crystals® instant coffee, 4.00 g of Lipton® tea, 1.50 g Copenhagen® snuff, 3.50 g Nestle® hot chocolate mix, and 1.70 g $FeCl_3$ (Fisher Scientific, reagent grade). The mixture is heated at 85° C. and stirred for 30 minutes. Thereafter, the mixture is filtered on No. 4 Whatman paper. After pouring the mixture onto the filter paper, 25 ml of isopropyl alcohol is poured over the filter cake, and the filter cake remains on vacuum for 15 minutes. The solids content of the filtrate is then determined by heating an aliquot at 200° C. for 25 minutes. The solids level is then reduced to 6 weight percent by diluting with 50% isopropyl alcohol in deionized water.

Ceramic discs (14 mm diameter×⅛" thick, Silamentin 60 discs available from Borges' Technical Ceramics) are washed in deionized water and dried overnight at 105° C. After drying, the discs are stored at 20° C. in 50% humidity (Constant temperature and humidity or CTH). Prior to staining, the discs are again heated to 105° C. for 1 hour followed by 1 hour at CTH. Using a Pasteur pipette, 132 $\mu$l of the stain prepared above is applied to one face of each disc and the disc is placed in an oven at 55° C. for 2 hours followed by heating in another oven at 120° C. for 16 hours. After heating, the discs are stored for 24 hours at CTH. During the storage period, the unstained face of the discs is coated with fast drying nail polish, such as Fast Dry Nail Enamel by New York Color.

The cleaning machine utilized is a Byk Chemie coating abrasion tester, catalog number AB-51115, that has been modified to hold 2 Oral-B No. 3 toothbrushes on each side. Two plexiglass plates, predrilled to hold 10, 14 mm discs, are mounted on each side of the cleaning machine. 10 previously stained discs are placed in each plexiglass plate and the plates placed in the cleaning machine. Two peristaltic pumps are connected to a beaker of deionized water, with each pump set to deliver 10 mls/min onto the disks, in a drop-wise manner, (1 pump/plexiglass plate) and the cleaning machine set to run for 10 complete strokes. The brush assembly is attached and the pumps and cleaning machine turned on. After 10 strokes, the discs are removed and dried for 10 minutes at 55° C. Whiteness, indicated by the Hunter L value, of each of the water-washed discs is then measured with an SP-62 spectrophotometer available from X-Rite Corporation using spherical specular included light. The values are recorded as the initial L value for each disc.

A solution of 0.1% xanthan gum and 1% glycerol in water is prepared. 100 g of toothpaste is added to a beaker containing 300 g of the xanthan gum-glycerol solution. This mixture is continuously stirred with a magnetic stir bar to prevent settling of the toothpaste. The beaker containing the toothpaste is placed on a stir plate and the tubing from the peristaltic pumps are placed inside the beaker. Water washed discs are placed in the plexiglass trays, the brush assembly attached, and the cleaning machine set for 800 strokes. The peristaltic pumps are turned on and when the toothpaste slurry begins dropping onto the discs at 10 ml/min, the brushing machine is turned on. After 800 brushing strokes, the discs are removed, rinsed, and dried at 55° C. for 10 minutes. The final L value of each disc is then measured on the spectrophotometer. The above water washing and brushing of 20 discs is repeated a second time to obtain a total of 40 discs for each toothpaste tested. The difference between the L value after water washing and the L value after brushing with toothpaste is the $\Delta L$ for that disc. The mean value for 40 discs is used to determine the $\Delta L$ for the toothpaste being tested.

After brushing, the pooled standard deviation of the data set is then calculated and must be less than 2.0 for the data to acceptable. Further, high cleaning and low cleaning commercial toothpastes, as determined by RDA, are run daily and serve as controls. The difference between the $\Delta L$ of the two controls must be greater than 10, as measured by HPCR, for the data to be accepted as reliable.

It will be appreciated that the staining concoction described herein for conducting the HPCR test method is representative in nature and the utility of this HPCR test method is not necessarily limited to that precise recipe. Approximations in amounts of the ingredients of the staining concoction are possible, and ingredient substitutions could be made for one or more of the ingredients thereof by substantially similar materials, to the extent that the test remains useful for indicating the cleaning effect of oral cleaning compositions of interest.

EXAMPLE 2

An aliquot of the wetcake used in Example 1 was diluted with an aqueous solution of tetrasodium pyrophosphate (TSPP), and then the resulting mixture was spray dried in a manner as described in Example 1. A free flowing composite particulate product was formed. After spray drying, the weight ratio of silica to TSPP was 99.375:0.625 in the composite product obtained. The material was then milled to a mean particle size of 10.33 $\mu$m, as measured by a Microtrac particle size analyzer, and had an Einlehner abrasion of 5.49 mg as measured by an Einlehner model 2000 instrument using brass screens as the substrate. The method consists of exposing a pre-weighed Fourdrinier brass wire screen to the action of a 10% aqueous silica suspension for 100,000 revolutions. The amount of abrasion is then determined as milligrams brass lost from the Fourdrinier wire screen.

When the silica-TSPP material is incorporated into toothpaste at a 16% loading level the resulting TSPP level is 0.1% of the toothpaste formulation. Chemical composition of Example 2 product is given in Table 1 below. This material was then formulated into toothpaste as described in Table 2 below. HPCR testing results, to determine the chemical cleaning effect of the toothpaste, are given in Table 3.

EXAMPLE 3

An aliquot of the wet cake used in example 1 was diluted with an aqueous solution of tetrasodium pyrophosphate (TSPP) such that after spray drying the resulting mixture the ratio of silica to TSPP in the dried composite particulate product was 93.75:6.25. The particulate material was then milled to a mean particle size of 8.45 $\mu$m and had an Einlehner abrasion of 6.2 mg. When the silica-TSPP material is added to the toothpaste at a 16% loading level the resulting TSPP level is 1.0% of the toothpaste formulation. Chemical composition of Example 3 product is given in Table 1 below. This material was then formulated into toothpaste as described in Table 2 below. HPCR testing results, to determine the chemical cleaning effect of the toothpaste, are given in Table 3.

EXAMPLE 4

An aliquot of the wet cake used in example 1 was diluted with an aqueous solution of tetrasodium pyrophosphate (TSPP) such that after spray drying the resulting mixture the ratio of silica to TSPP in the dried composite particulate product was 62.5:37.5. The material was then milled to a mean particle size of 9.3 $\mu$m and had an Einlehner abrasion of 7.1 mg. When the silica-TSPP material is added to the toothpaste at a 16% loading level the resulting TSPP level is 6.0% of the toothpaste formulation. Chemical composition of Example 4 product is given in Table 1 below. This material was then formulated into toothpaste as described in Table 2 below. HPCR testing results, to determine the chemical cleaning effect of the toothpaste, are given in Table 3.

TABLE 1

| Sample | % $H_2O$ | % LOI | % $SiO_2$ | % $SO_3$ | % $Na_2O$ | % $P_2O_5$ |
|---|---|---|---|---|---|---|
| Example 2 | 6.99 | 4.16 | 94.17 | 0.38 | 0.87 | 0.16 |
| Example 3 | 7.55 | 4.20 | 91.37 | 0.43 | 2.07 | 1.50 |
| Example 4 | 6.68 | 3.94 | 75.89 | 0.35 | 9.50 | 10.32 |

Table 1 Glossary:
$H_2O$ was determined by heating for 2 hours at 105° C.
LOI was determined by heating for 2 hours at 900° C.
$SiO_2$ was determined by dissolution in HF.
$SO_3$ was determined using a LECO sulfur analyzer.
$Na_2O$ and $P_2O_5$ were determined by an ICP spectrophotometer.

Table 1 lists the chemical composition of examples 2–4. The phosphate concentrations, expressed as $P_2O_5$ were calculated from phosphorus determination utilizing Inductively Coupled Plasma (ICP) Spectroscopy. The increase in phosphorous content is a direct result of the increasing amount of TSPP added to each example. The increase in the Na$_2$O of 0.87% in example 2, to 9.50% in example 4, is due to the contribution of sodium from addition of TSPP as the chemical cleaning agent in these examples. All other values reported are typical for dental grade silicas.

Toothpaste formulations are prepared with the inventive silicas and control silicas according to the method described below incorporating the amounts of ingredients given in Table 2.

Toothpaste Preparation

The glycerin, sodium carboxymethyl cellulose, polyethylene glycol and sorbitol are mixed together and stirred until the ingredients are dissolved to form a first admixture. The deionized water, sodium fluoride, any phosphate or pyrophosphate added neat, and sodium saccharin are also mixed together and stirred until these ingredients are dissolved to form a second admixture. These two admixtures are then combined with stirring. Thereafter, color is added with stirring to obtain a "pre-mix".

The pre-mix is placed in a Ross mixer (Model 130 LDM) and silica abrasive and titanium dioxide are mixed in, without vacuum. A 30-inch vacuum is drawn and the resultant admixture is stirred for approximately 15 minutes. Lastly, sodium lauryl sulfate and flavor are added and the admixture is stirred for approximately 5 minutes at a reduced mixing speed.

Toothpaste Formulations were prepared using Examples 1–4 silicas. Toothpaste 1 contains Example 1 silica with no added Ad pyrophosphate. Toothpastes 2, 4 and 6 contain the inventive silica-chemical cleaning agent combinations of Examples 2, 3 and 4, respectively. To each of these toothpastes was added a quantity of Example 1 silica corresponding to the amount of pyrophosphate utilized to make the total silica abrasive content 16%. Toothpastes 3, 5 and 7 are comparative toothpastes for toothpastes 2, 4 and 6, respectively, containing 16% Example 1 silica and TSPP added in the conventional manner at the same percentage as the corresponding toothpastes.

Table 7 were evaluated using the HPCR test one week after toothpaste formulation. Results are given in Table 3 below.

TABLE 3

| Toothpaste No. | HPCR 1 week |
|---|---|
| 1 control | 0.52 |
| 2 inventive | 6.27 |
| 3 comparison | 2.44 |
| 4 inventive | 15.8 |
| 5 comparison | 12.82 |
| 6 inventive | 18.01 |
| 7 comparison | 23.86 |

In toothpastes 2 and 4, improved cleaning is seen when TSPP is incorporated into the silica rather than added neat to the toothpaste formulation, as is done in comparative toothpastes 3 and 5. The improved cleaning, as measured by the HPCR test, ranges from a 157% improvement when 0.1% TSPP is used to 23% when 1% TSPP is used. At a 6% level, improvement was not seen, however substantial cleaning was observed.

EXAMPLE 5

To prepare the precipitated silica of this example, 87.1 liters of water are added to a steam-jacketed reactor, which is equipped with high shear mixing blades, and heated to 88° C. 7.5 liters of sodium silicate solution, 13.3% (2.65 mole ratio), preheated to 85° C. are added to the reactor. Immediately thereafter, preheated sodium silicate solution (10 l/min) and 11.4% sulfuric acid solution at ambient temperature (5.1 l/min) are added simultaneously with mixing. Simultaneous addition of the silicate and acid continues for 60 minutes, at which time the silicate addition is stopped and acid addition continues until a pH of 5.3 is attained. Next, the temperature of the reaction media is increased to 93° C. for 5 minutes while maintaining the pH. Thereafter, the resultant precipitated silica mass is transferred to a rotary

TABLE 2

| | Toothpastes Tested | | | | | | |
|---|---|---|---|---|---|---|---|
| Toothpaste Formulations | Toothpaste 1 | Toothpaste 2 | Toothpaste 3 | Toothpaste 4 | Toothpaste 5 | Toothpaste 6 | Toothpaste 7 |
| Glycerin, 99.5% | 11.000 | 11.000 | 11.000 | 11.000 | 11.000 | 11.000 | 11.000 |
| Sorbitol, 70.0% | 43.807 | 43.702 | 43.702 | 43.175 | 43.175 | 39.807 | 39.807 |
| Deionized Water | 22.000 | 22.005 | 22.005 | 21.632 | 21.632 | 20.000 | 20.000 |
| Carbowax 600[a] | 3.000 | 3.000 | 3.000 | 3.000 | 3.000 | 3.000 | 3.000 |
| CMC-7MXF[b] | 1.400 | 1.400 | 1.400 | 1.400 | 1.400 | 1.400 | 1.400 |
| Tetrasodium Pyrophosphate[c] | 0 | 0 | 0.100 | 0 | 1.000 | 0 | 6.000 |
| Sodium Saccharin | 0.200 | 0.200 | 0.200 | 0.200 | 0.200 | 0.200 | 0.200 |
| Sodium Fluoride | 0.243 | 0.243 | 0.243 | 0.243 | 0.243 | 0.243 | 0.243 |
| Ex. 1 control silica | 16.000 | 0.100 | 16.000 | 1.000 | 16.000 | 6.000 | 16.000 |
| Ex. 2 | 0 | 16.000 | 0 | 0 | 0 | 0 | 0 |
| Ex. 3 | 0 | 0 | 0 | 16.000 | 0 | 0 | 0 |
| Ex. 4 | 0 | 0 | 0 | 0 | 0 | 16.000 | 0 |
| TiO$_2$ | 0.500 | 0.500 | 0.500 | 0.500 | 0.500 | 0.500 | 0.500 |
| Sodium Lauryl Sulfate | 1.200 | 1.200 | 1.200 | 1.200 | 1.200 | 1.200 | 1.200 |
| Flavor | 0.650 | 0.650 | 0.650 | 0.650 | 0.650 | 0.650 | 0.650 |
| Total | 100.000 | 100.000 | 100.000 | 100.000 | 100.000 | 100.000 | 100.000 |

[a]: Carbowax 600 is polyethylene glycol available from Union Carbide, Danbury, CT
[b]: CMC-7MXF is a sodium carboxymethyl cellulose available from Aqualon, a division of Hercules Corp., Wilmington, DE.
[c]: Pyrophosphate added neat drum filter for filtration and washing. This dewatered material is referred to as a "wet cake". The silica wet cake, containing abrasive silica with an Einlehner abrasion value of 5.36, was adjusted to a solids content of 15% with water as the diluent. The resulting silica slurry was spray dried in an ANHYDRO spray drier with an inlet temperature of 350° C. and then milled in a RAYMOND hammer mill to a mean particle size of 11.55 µm. The resulting silica was then formulated into toothpaste as described in Table 5 below. HPCR testing results, to determine the chemical cleaning effect of the toothpaste, are given in Table 6.

EXAMPLE 6

An aliquot of the wet cake prepared in example 5 was diluted with a solution of sodium tripolyphosphate (STPP) such that after spray drying the resulting mixture the ratio of silica to STPP in the dried composite particulate product was 99.375:0.625. The material was then milled to a mean particle size of 11.25 µm and had an Einlehner abrasion of 5.6 mg. When the silica-STPP material is added to the toothpaste at a 16% loading level the resulting STPP level is 0.1% of the toothpaste formulation. Chemical composition of Example 6 product is given in Table 4 below. This material was then formulated into toothpaste as described in Table 5 below. HPCR testing results, to determine the chemical cleaning effect of the toothpaste, are given in Table 6.

EXAMPLE 7

An aliquot of the wet cake prepared in example 5 was diluted with a solution of STPP such that after spray drying the resulting mixture the ratio of silica to STPP in the dried composite particulate product was 93.75:6.26. The material was then milled to a mean particle size of 10.94 µm and had an Einlehner abrasion of 5.5 mg. When the silica-STPP material is added to the toothpaste at a 16% loading level the resulting STPP level is 1.0% of the toothpaste formulation. Chemical composition of Example 7 product is given in Table 4 below. This material was then formulated into toothpaste as described in Table 5 below. HPCR testing results, to determine the chemical cleaning effect of the toothpaste, are given in Table 6.

EXAMPLE 8

An aliquot of the wet cake prepared in example 5 was diluted with a solution of STPP such that after spray drying the resulting mixture the ratio of silica to STPP in the dried composite particulate product was 62.5:37.5. The material was then milled to a mean particle size of 12.28 µm and an Einlehner abrasion of 5.1 mg. When the silica-STPP material is added to the toothpaste at a 16% loading level the resulting STPP level is 1.0% of the toothpaste formulation. The chemical analyses results of the compositions of Examples 6, 7 and 8 product are given in Table 4 below. These materials were then formulated into toothpastes as described in Table 5 below. HPCR testing results, to determine the chemical cleaning effect of the toothpaste, are given in Table 6.

TABLE 4

| Sample | % $H_2O$ | % LOI | % $SiO_2$ | % $SO_3$ | % $Na_2O$ | % $P_2O_5$ |
|---|---|---|---|---|---|---|
| Example 6 | 3.93 | 3.47 | 94.93 | 0.45 | 0.84 | 0.20 |
| Example 7 | 4.30 | 3.73 | 91.42 | 0.48 | 2.31 | 2.17 |
| Example 8 | 6.13 | 4.09 | 69.62 | 0.40 | 10.86 | 13.74 |

Toothpaste Formulations were prepared using Examples 5–8 silicas. Toothpaste 8 contains Example 5 silica with no added STPP. Toothpastes 9, 11 and 13 contain the inventive silica-chemical cleaning agent combinations of Examples 6, 7 and 8, respectively. To each of these toothpastes was added a quantity of Example 5 silica corresponding to the amount of STPP utilized to make the total silica abrasive content 16%. Toothpastes 10, 12 and 14 are comparative toothpastes for toothpastes 9, 11 and 13, respectively, containing 16% Example 1 silica and STPP added in the conventional manner at the same percentage as the corresponding toothpastes.

TABLE 5

| | Toothpastes Tested | | | | | | |
|---|---|---|---|---|---|---|---|
| Toothpaste Formulations | Toothpaste 8 | Toothpaste 9 | Toothpaste 10 | Toothpaste 11 | Toothpaste 12 | Toothpaste 13 | Toothpaste 14 |
| Glycerin, 99.5% | 11 | 11 | 11 | 11 | 11 | 11 | 11 |
| Sorbitol, 70.0% | 43.807 | 43.702 | 43.702 | 42.802 | 42.802 | 39.802 | 39.807 |
| Deionized Water | 22 | 22.005 | 22.005 | 22.005 | 22.005 | 22 | 20 |
| Carbowax 600 | 3 | 3 | 3 | 3 | 3 | 3 | 3 |
| CMC-7MXF | 1.4 | 1.4 | 1.4 | 1.4 | 1.4 | 1.4 | 1.4 |
| Sodium Saccharin | 0.2 | 0.2 | 0.2 | 0.2 | 0.2 | 0.2 | 0.2 |
| Sodium Fluoride | 0.243 | 0.243 | 0.243 | 0.243 | 0.243 | 0.243 | 0.243 |
| Tripolyphosphate[d] | 0 | 0 | 0.1 | 0 | 1 | 0 | 6 |
| Ex. 5 control | 16 | 0.1 | 16 | 1 | 16 | 6 | 16 |
| Ex. 6 | 0 | 16 | 0 | 0 | 0 | 0 | 0 |
| Ex. 7 | 0 | 0 | 0 | 16 | 0 | 0 | 0 |
| Ex. 8 | 0 | 0 | 0 | 0 | 0 | 16 | 0 |
| $TiO_2$ | 0.5 | 0.5 | 0.5 | 0.5 | 0.5 | 0.5 | 0.5 |
| Sodium Lauryl Sulfate | 1.2 | 1.2 | 1.2 | 1.2 | 1.2 | 1.2 | 1.2 |
| Flavor | 0.65 | 0.65 | 0.65 | 0.65 | 0.65 | 0.65 | 0.65 |
| Total | 100 | 100 | 100 | 100 | 100 | 100 | 100 |

[d]: STPP added neat.

Each of the above prepared seven toothpastes were evaluated using the HPCR test one week and 3 months after toothpaste formulation. Results are given in Table 6 below.

TABLE 6

| Toothpaste No. | HPCR 1 week | HPCR 3 months |
|---|---|---|
| 8 control | 0.52 | 2.34 |
| 9 inventive | 4.39 | 0.71 |
| 10 comp. | 1.83 | −3.01 |
| 11 inventive | 12.72 | 12.03 |
| 12 comp. | 4.42 | 6.99 |
| 13 inventive | 21.29 | 20.64 |
| 14 comp. | 12.33 | 12.16 |

The 1-week results for toothpaste nos. 9–14 are shown in bar graphs depicted in FIG. 1. At one week, improved cleaning is seen for toothpastes 9, 11 and 13 where STPP is incorporated via the silica rather than added neat to the toothpaste formulation, as is done in comparative toothpastes 10, 12 and 14. The improved cleaning, as measured by the HPCR test, is 140% improvement when 0.1% STPP is used, 188% when 1.0% STPP is used and 73% when 6.0% STPP is used.

The above toothpastes were stored at room temperature for 3 months and HPCR testing repeated to determine storage stability. As was seen in the freshly prepared toothpastes, the three-month HPCR results of the present invention chemical cleaning silicas show substantial improvements versus the comparative toothpaste formulations.

EXAMPLE 9

To prepare the precipitated silica of this example, 515 gallons of sodium silicate, 13.0% (2.65 mole ratio) solution are added to a steam-jacketed reactor, which is equipped with high shear mixing blades, and heated to 190° F. After the reactor reaches the desired temperature, 13.0% silicate solution preheated to 185° F. and 11.4% sulfuric acid solution at ambient temperature are added simultaneously at a rate of 102.9 and 45.2 gpm, respectively. Simultaneous addition of the silicate and acid continues for 47 minutes with agitation. After 47 minutes the sodium silicate addition is stopped, while the acid addition continues until the reaction mixture reaches a pH of 5.8–6.0. When the pH reaches 5.8 to 6.0, the temperature of the reaction media is increased to 199° F. for 20 minutes, while maintaining the pH. Thereafter, the resultant precipitated silica reaction mass is transferred to a rotary drum filter for filtration and washing. This dewatered material is referred to as a "wet cake". The silica wet cake, containing abrasive silica with an Einlehner abrasion value of 5.04, was adjusted to a solids content of 15% with water as the diluent. The resulting silica slurry was spray dried in an ANHYDRO spray drier with an inlet temperature of 350° C. and then milled in a Jet Pulveriser air mill to a mean particle size of 11.55 μm. The resulting silica was then formulated into toothpaste in the formulation Table 8 below. HPCR testing results, to determine the chemical cleaning effect of the toothpaste, are given in Table 9.

EXAMPLE 10

An aliquot of the wet cake used in example 9 was diluted with a solution of TKPP such that after spray drying the resulting mixture the ratio of silica to TKPP in the dried composite particulate product was 99.375:0.625. The material was then milled to a mean particle size of 10.97 μm and an Einlehner abrasion of 5.8 mg. When the silica-TKPP material is added to the toothpaste at a 16% loading level the resulting TKPP level is 0.1% of the toothpaste formulation. Chemical composition of Example 10 product is given in Table 7 below. This material was then formulated into toothpaste, as described in Table 8 below. HPCR testing results, to determine the chemical cleaning effect of the toothpaste, are given in Table 9.

EXAMPLE 11

An aliquot of the wet cake used in example 9 was diluted with a solution of tetrapotassium pyrophosphate (TKPP) such that after spray drying the resulting mixture the ratio of silica to TKPP in the dried composite particulate product was 93.75:6.26. The material was then milled to a mean particle size of 10.77 μm and an Einlehner abrasion of 5.2 mg. When the silica-TKPP material is added to the toothpaste at a 16% loading level the resulting TKPP level is 1.0% of the toothpaste formulation. Chemical composition of Example 11 product is given in Table 7 below. This material was then formulated into toothpaste, as described in Table 8 below. HPCR testing results, to determine the chemical cleaning effect of the toothpaste, are given in Table 9.

EXAMPLE 12

An aliquot of the wet cake used in example 9 was diluted with a solution of TKPP such that after spray drying the resulting mixture the ratio of silica to TKPP in the dried composite particulate product was 62.5:37.5. The material was then milled to a mean particle size of 10.99 μm and an Einlehner abrasion of 5.2 mg. When the silica-TKPP material is added to the toothpaste at a 16% loading level the resulting TKPP level is 6.0% of the toothpaste formulation. Chemical composition of Example 12 product is given in Table 7 below. This material was then formulated into toothpaste, as described in Table 8 below. HPCR testing results, to determine the chemical cleaning effect of the toothpaste, are given in Table

TABLE 7

| Sample | % $H_2O$ | % LOI | % $SiO_2$ | % $SO_3$ | % $Na_2O$ | % $K_2O$ | % $P_2O_5$ |
|---|---|---|---|---|---|---|---|
| Example 10 | 4.52 | 3.17 | 95.27 | 0.45 | 0.62 | 0.24 | 0.16 |
| Example 11 | 4.15 | 3.46 | 91.52 | 0.45 | 0.64 | 2.24 | 1.59 |
| Example 12 | 89 | 3.64 | 73.45 | 0.38 | 1.72 | 12.38 | 9.71 |

Toothpaste Formulations were prepared using Examples 9–12 silicas. Toothpaste 15 contains Example 9 silica with no added TKPP. Toothpastes 16, 18 and 20 contain the inventive silica-chemical cleaning agent combinations of Examples 10, 11 and 12, respectively. To each of these toothpastes was added a quantity of Example 9 silica corresponding to the amount of TKPP utilized to make the total silica abrasive content 16%.

Toothpastes 17, 19 and 21 are comparative toothpastes for toothpastes 16, 18 and 20, respectively, containing 16% Example 9 silica and TKPP added in the conventional manner at the same percentage as the corresponding toothpastes.

TABLE 8

| | Toothpaste 15 | Toothpaste 16 | Toothpaste 17 | Toothpaste 18 | Toothpaste 19 | Toothpaste 20 | Toothpaste 21 |
|---|---|---|---|---|---|---|---|
| Glycerine, 99.5% | 11 | 11 | 11 | 11 | 11 | 11 | 11 |
| Sorbitol, 70.0% | 43.807 | 43.702 | 43.702 | 42.802 | 42.802 | 39.807 | 39.807 |
| Deionized Water | 22 | 22.005 | 22.005 | 22.005 | 22.005 | 20 | 20 |
| Carbowax 600 | 3 | 3 | 3 | 3 | 3 | 3 | 3 |
| CMC-7MXF | 1.4 | 1.4 | 1.4 | 1.4 | 1.4 | 1.4 | 1.4 |
| Sodium Saccharin | 0.2 | 0.2 | 0.2 | 0.2 | 0.2 | 0.2 | 0.2 |
| Sodium Fluoride | 0.243 | 0.243 | 0.243 | 0.243 | 0.243 | 0.243 | 0.243 |
| TKPP[e] | 0 | 0 | 0.1 | 0 | 1 | 0 | 6 |
| Example 9 | 16 | 0.1 | 16 | 1 | 16 | 6 | 16 |
| Example 10 | 0 | 16 | 0 | 0 | 0 | 0 | 0 |
| Example 11 | 0 | 0 | 0 | 16 | 0 | 0 | 0 |
| Example 12 | 0 | 0 | 0 | 0 | 0 | 16 | 0 |
| $TiO_2$ | 0.5 | 0.5 | 0.5 | 0.5 | 0.5 | 0.5 | 0.5 |
| Sodium Lauryl Sulfate | 1.2 | 1.2 | 1.2 | 1.2 | 1.2 | 1.2 | 1.2 |
| Flavor | 0.65 | 0.65 | 0.65 | 0.65 | 0.65 | 0.65 | 0.65 |
| Total | 100 | 100 | 100 | 100 | 100 | 100 | 100 |

[e]: Condensed phosphate added neat.

Each of the above prepared seven toothpastes were evaluated using the HPCR test one week after toothpaste formulation. Results are given in Table 9 below.

TABLE 9

| Toothpaste No. | HPCR 1 week |
|---|---|
| 15 control | 8.58 |
| 16 inventive | 7.39 |
| 17 comp. | 12.88 |
| 18 inventive | 13.71 |
| 19 comp. | 14.09 |
| 20 inventive | 18.24 |
| 21 comp. | 15.12 |

At one week, improved cleaning is seen for toothpaste 20 where TKPP is incorporated into the silica at a 6% level rather than added neat to the toothpaste formulation, as is done in comparative toothpaste 21. The improved cleaning, as measured by the HPCR test, is 21% improvement when 6% TKPP is used, however, at lower loading levels improvement is not seen.

As observed in experimental studies described herein, dentifrices including the surface-modified silicas according to the invention provide higher cleaning efficacy than dentifrices including unmodified silica with or without the same cleaning agent added neat, i.e., as a freely dispersed ingredient, to dentifrice formulation. In particular, the surface-modified silicas of the invention more effectively deliver the cleaning agents directly and assuredly onto and against the teeth during the brushing process than the presence of only freely dispersed forms of the same cleaning agent in a dentifrice. This results in whiter teeth. For instance, improvements between 5% and 188% in whiteness have been observed with toothpastes incorporating the surface-modified silica according to the present invention as compared to that observed for comparison toothpastes using freely dispersed chemical cleaning agents in unmodified silica-containing toothpastes.

Thus, a synergistic or unique type of cleaning effect is observed to occur when cleaning teeth using the synthetic silicas surface-modified with cleaning agent according to this invention. Although not desiring to be bound to any particular theory at this time, one possible mechanism of action is thought due to the intimate and direct physical contact of the silica and cleaning agent concomitantly with the teeth that is made possible by the inventive surface-modified, composite particles, allowing for increased chelation of metals and/or detergent action by the chemical cleaning agents during polishing, which yields whiter teeth. Another advantage of this invention is that lower concentrations of the cleaning agent can be used to provide equivalent cleaning as compared to that of dentifrices using higher concentrations of the same cleaning agent added in the conventional neat manner.

EXAMPLE 13

The HPCR cleaning test was compared to the conventional PCR test to assess their relative predictivity in measuring cleaning efficacy for stained teeth when cleaned with the same toothpastes. The Pellicle Cleaning Ratio (PCR) cleaning values were determined by the PCR test described in "In Vitro Removal of Stain With Dentifrice", G. K. Stookey, et al., J. Dental Res., 61, 1236–9, 1982. The HPCR cleaning values were determined according to the procedure described above in Example 1.

Figure 2:
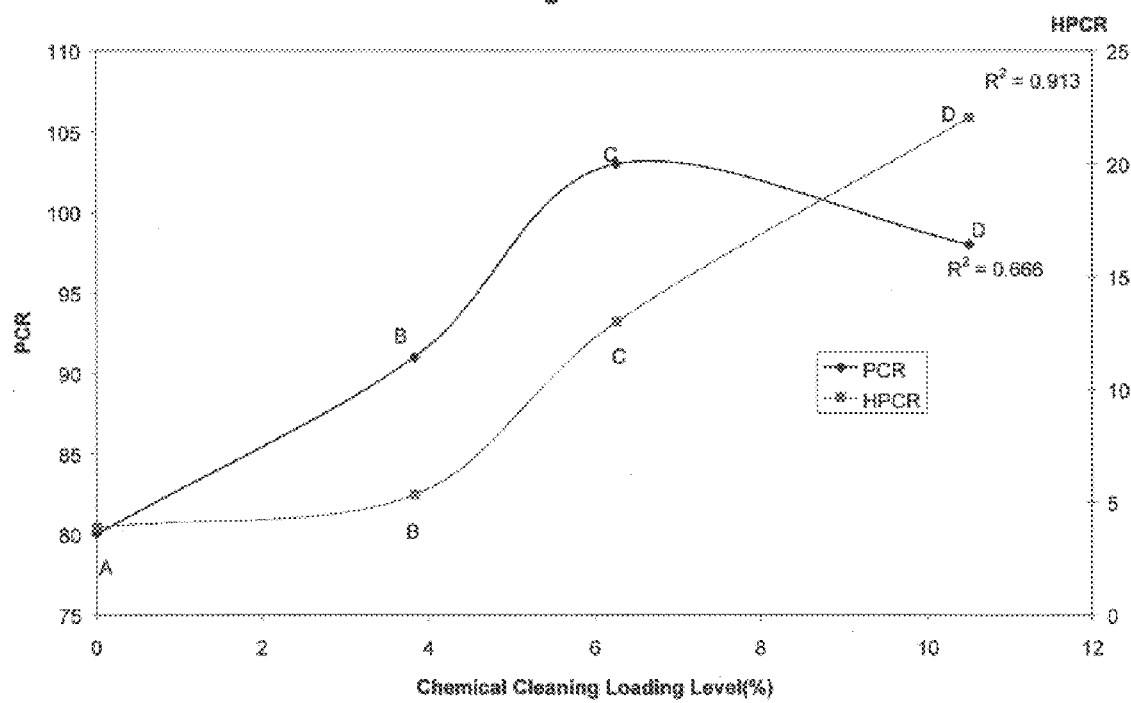
FIG. 2 graphically shows the results of certain experimental studies described in the examples herein comparing the cleaning action measured by HPCR and separately PCR observed for commercial dentifrices not containing the surface-modified silica according to an aspect of this invention.

FIG. 2 graphically compares the results between PCR and HPCR of four different commercial toothpastes, labeled in FIG. 2 as toothpastes A, B, C and D, which contained 0% (toothpaste A), 3.8% (toothpaste B), 6.2% (toothpaste C) and 7.8% (toothpaste D), respectively, of condensed phosphate chemical cleaning component. Commercial toothpaste "A" was CREST, toothpaste "B" was CREST MULTICARE, commercial toothpaste "C" was AQUAFRESH WHITENING, and commercial toothpaste "D" was CREST TARTAR CONTROL.

The concentration of the condensed phosphate chemical cleaning agents in each of toothpastes A, B, C and D was determined by ICP analysis, which directly determined the phosphorus content from which diphosphorus pentaoxide ($P_2O_5$) content could be calculated.

As can be seen from FIG. 2, there was a poor correlation between the PCR test and the level of condensed phosphate chemical cleaning agents in commercial toothpastes. On the other hand, a good correlation existed between the HPCR test and the level of condensed phosphate chemical cleaning agents in commercial toothpastes. The correlation coefficient for PCR versus chemical cleaning agent loading level is 0.5738, meaning there is little if any correlation between the PCR test and the amount of chemical cleaning agent in the toothpaste. By contrast, the HPCR test for determining chemical cleaning has a cleaning correlation coefficient of 0.9189 indicating a strong correlation between the chemical cleaning agent concentration and the HPCR test. These results clearly indicated that the HPCR test is a better test than PCR for measuring the chemical cleaning functionality of a dentifrice.

While the invention has been described in terms of its preferred embodiments, those skilled in the art will recognize that the invention can be practiced with modification within the spirit and scope of the appended claims.

What is claimed is:

1. A composition of matter comprising particles of precipitated silica, where the precipitated silica particles have surfaces at which condensed alkali metal phosphate is retained, wherein the composition comprises about 30 to about 99.9 wt % precipitated silica and from about 0.1 to about 70 wt % condensed alkali metal phosphate, and wherein the precipitated silica particles have an average particle size between about 0.1 to about 80 µm, a void volume value in the range of about 1.0 to about 4.0 cc/g, and an acceptable Einlehner abrasion value.

2. The composition of claim 1, wherein the silica surfaces comprise land areas and pores, where at least a portion of the condensed phosphate is retained at the land areas.

3. The composition of claim 1, wherein the silica surfaces comprise land areas and pores, where the pores contain at least a portion of the condensed phosphate.

4. The composition of claim 1, wherein the condensed phosphate is selected from the group consisting of tetraalkaii metal pyrophosphate, dialkali metal diacid pyrophosphate, trialkali metal monoacid pyrophosphate, pentaalkali metal tripolyphosphate, and alkali metal polymetaphosphate, singly or in combinations thereof.

5. The composition of claim 1, wherein the condensed phosphate is selected from the group consisting of tetrasodium pyrophosphate, tetrapotassium pyrophosphate, disodium dihydrogen pyrophosphate, trisodium monohydrogen pyrophosphate, pentasodium tripolyphosphate and sodium polymetaphosphate, singly or in combinations thereof.

6. The composition of matter of claim 1, wherein the composition comprises about 60 to about 95 wt % silica and from about 5 to about 40 wt % condensed phosphate.

7. The composition of claim 1, wherein the silica has a mean particle size of about 0.1 to about 30 µm.

8. A composition of matter comprising particles of precipitated silica, where the precipitated silica particles have surfaces at which condensed alkali metal phosphate is retained, wherein the precipitated silica particles are obtained from a dispersion of a wet cake of precipitated silica in an aqueous solution containing a dissolved alkali metal salt of a condensed phosphate whereupon the dispersion is spray dried effective to provide the association of condensed alkali metal phosphate to the surfaces of the precipitated silica particles, wherein the composition comprises about 30 to about 99.9 wt % precipitated silica and from about 0.1 to about 70 wt % condensed alkali metal phosphate, and wherein the precipitated silica particles have an average particle size between about 0.1 to about 80 µm, a void volume value in the range of about 1.0 to about 4.0 cc/g, and an acceptable Einlehner abrasion value.

9. The composition of matter of claim 1, whereon the composition comprises about 93.75 to about 99.375 wt % precipitated silica and from 0.625 to 6.25 wt % condensed alkali metal phosphate.

* * * * *